United States Patent [19]

Disteldorf et al.

[11] Patent Number: 4,549,991

[45] Date of Patent: Oct. 29, 1985

[54] PROCESS FOR CONTINUOUS HOT PHOSGENATION OF AMINES

[75] Inventors: Josef Disteldorf; Werner Hübel, both of Herne; Johannes Reiffer, Essen, all of Fed. Rep. of Germany

[73] Assignee: Chemische Werke Huls Aktiengesellschaft, Marl, Fed. Rep. of Germany

[21] Appl. No.: 540,997

[22] Filed: Oct. 11, 1983

[30] Foreign Application Priority Data

Oct. 9, 1982 [DE] Fed. Rep. of Germany ....... 3237541
Jul. 2, 1983 [DE] Fed. Rep. of Germany ....... 3323882

[51] Int. Cl.⁴ .............................................. C07C 69/00
[52] U.S. Cl. .......................... 260/453 PH; 260/453 P
[58] Field of Search ...................... 260/453 PH, 453 P

[56] References Cited

U.S. PATENT DOCUMENTS 3,829,458  8/1974  Horn et al. .................. 260/453 PH
4,092,343  5/1978  Frulla .......................... 260/453 PH
4,128,569  12/1978 Horn et al. .................. 260/453 PH

FOREIGN PATENT DOCUMENTS 1165587  12/1962  Fed. Rep. of Germany .
1568844  6/1966   Fed. Rep. of Germany .
1792660  9/1968   Fed. Rep. of Germany .

OTHER PUBLICATIONS

"Ullmanns Encyclopaedic der teshnischen Chemie", Fourth Edition, vol. 13, p. 350 ff.

*Primary Examiner*—Alan Siegel
*Attorney, Agent, or Firm*—Oblon, Fisher, Spivak, McClelland & Maier

[57] ABSTRACT

This invention relates to a process for the production of organic isocyanates by the continous hot phosgenation of amines, whereby the solids are retained in the reactor by an appropriate separator and the isocyanate formed during the reaction is constantly removed from the reactor. Preferably the amount of solids of the suspension in the reactor is set so that the amount of the isocyanate taken off per unit of time reaches a maximum.

12 Claims, No Drawings

PROCESS FOR CONTINUOUS HOT PHOSGENATION OF AMINES

BACKGROUND OF THE INVENTION

1. Field of the Invention

This invention relates to an improved process for the preparation of organic isocyanates. More specifically, organic isocyanates are produced by a continuous hot phosgenation process which results in purer products in higher yields than previously achieved.

2. Description of the Prior Art

The majority of organic isocyanates is produced by phosgenation of primary amines, their hydrochlorides or their carbonamide acid salts, see, e.g., "Ullmanns Encyclopaedie der technischen Chemie," fourth edition, Vol. 13, p. 350 ff.

The so-called based phosgenation is technically the most important process. In a cold state, the amine present in an inert solvent reacts with excess phosgene in solution (cold phosgenation) according to the following reaction:

$$2RNH_2 + COCl_2 \rightarrow R-NH-CO-Cl + R-NH_3^+Cl^-$$

In the second step, the so-called hot phosgenation, carbamoyl chloride dehydrochlorinates at temperatures above 80° C. to give hydrogen chloride and the desired isocyanate $R-NH-CO-CL \rightarrow RNCO + HCL$ and the hydrochloride is converted into the isocyanate $$R-NH_3^+Cl^- + COCL_2 \rightarrow RNCO + 3HCl$$

The two reactions can be summarized up as follows:

$$R-NH-CO-Cl + R-NH_3^+Cl^- + COCl_2 \rightarrow 2R-NCO + 4HCl$$

A problem encountered in the above-described process is that there is a competitive reaction to isocyanate formation. The amine reactant and the already formed carbamoyl chloride or the isocyanate can react to form urea according to the following scheme.

$$R-NHCOCl + R-NH_2 \rightarrow R-NH-CO-NH-R + HCl$$

$$R-NCO + R-NH_2 \rightarrow R-NH-CO-NH-R$$

Depending on the specific amine, the ureas are converted into isocyanate only with great difficulty or not at all. This applies especially to aliphatic amines and particularly to polyamines. Therefore, the process must be conducted so that urea formation is prevented.

To avoid these problems it is necessary to conduct the prephosgenation reaction in preferably a large excess of phosgene and at temperatures as low as possible. Therefore, in practice a relatively concentrated phosgene solution in excess is used and the amine is added in an organic solvent.

It is critical that the amine be dispersed in the phosgene solution as quickly as possible. Therefore, special mixing devices are required. It is emphasized that it is important for the prevention of the secondary reaction of the amine with already formed isocyanates "that every single amine molecule introduced into the process would have to be immediately surrounded by phosgene before it gets into contact with any formed isocyanate molecules" (DE-PS No. 17 92 660, column 3, lines 15-19). This is practically impossible to achieve. The most effective mixing units are mixing nozzles. However, clogging and deposits of solids occur in the mixing nozzles which interfere with the mixing process.

Moreover, due to the fact that a concentrated phosgene solution is necessary, considerable effort is required to dissipate the reaction heat formed in the strongly exothermic reaction which occurs at a relatively low temperature level. Practically speaking, the operation is continuously adiabatic, i.e., at a relatively high temperature (cf. DE-PS No. 11 65 587). In addition, conducting the reaction in and maintaining a highly concentrated phosgene solution is questionable from a safety aspect. Despite the foregoing disadvantages, most aromatic amines are base-phosgenated to form isocyanates.

On the other hand, aliphatic amines, which are more strongly basic, are even more difficult to phosgenate directly as a base. Urea formation can, however, be more easily prevented if the carbamic acid salt of the amine is used in the prephosgenation step instead of the free amine.

In the so-called carbamate process, the carbamic acid salt is first prepared by saturating an amine solution with carbon dioxide as follows, $$2RNH_2 + CO_2 \rightarrow R-N^{30}H_3 \, O^-OC-NH-R,$$

which salt is difficult to dissolve and is suspended in the solvent. In the subsequent cold phosgenation, the same carbamoyl chloride-hydrochloride mixture is formed while giving off $CO_2$. As with the standard base phosgenation process, the cold reaction is similarly followed by hot phosgenation according to the following scheme:

$$R-NH-COO^-H_3N^+-R + COCl_2 \rightarrow R-NH-COCl + R-N^+H_3C^-l + CO_2$$

$$R-NH-CO-Cl + RN^+H_3Cl^- + COCl_2 \rightarrow 2R-NCO + 4HCl$$

The above carbamate process does permit a smaller input in mixing the amine or its carbamate with phosgene. However, the disadvantage is that a third reaction stage is necessary and in addition $CO_2$ is required which can only be recovered from the exhaust gas at considerable effort and cost.

The most effective method to prevent urea formation is to follow the so-called hydrochloride method and to phosgenate the hydrochloride a follows:

$$R-N^+H_3Cl^- + COCl_2 \rightarrow RNCO + 3HCl$$

The disadvantages of this process is that stable hydrochlorides are formed, which do not react in the cold state and even when heated their reaction rate is comparatively slow. Therefore, either long reaction times or higher temperatures necessary to reduce the duration of the reaction are required which lead to undesirable secondary reactions, such as chlorine substitution and isocyanate polymerization. Thus, it is more difficult to conduct this reaction on a continuous basis.

A typical procedure for such a phosgenation process is described in DE-OS No. 15 68 844. It is described that the hydrochloride suspension of an organic amine is phosgenated in several stages at an elevated temperature in a stirring cascade until a clear reaction solution flows off.

To illustrate the resulting difficulties, of the hydrochloride method, the phosgenation of 1,5-diamino-2-methylpentane is cited. This process is disclosed in U.S. Pat. No. 3,631,198, which indicates that the corresponding diisocyanate is isolated with a yield of only 19% under conditions in which the analogous hexamethylenediisocyanate is obtained with a 95% yield. According to the this U.S. patent, the yield can be raised to 82.7% by using diethylphthalate; however, the disadvantage of this solvent is that its boiling point is close to that of the diisocyanate which has been obtained and thus it is difficult to separate the solvent. Moreover, this solvent is not sufficiently stable under the reaction conditions described. Phthalic acid anhydride is formed which precipitates in a crystalline form and, in turn, creates a troublesome by-product.

In view of the foregoing, it is apparent that a serious need exists for an improved process for the preparation of organic isocyanates from amines.

SUMMARY OF THE INVENTION

In accordance with the present invention it has been discovered that organic isocyanates can be prepared by a single stage, continuous hot phosgenation step. The process of the invention is a modification of the above-described hydrochloride method wherein the reaction time has been reduced and purer products in higher yields have been achieved compared to the previously described processes.

It has now been found that the process of hot phosgenation in a continuous operation can be considerably improved by retaining the solids in the reactor with the aid of a suitable separator and further, by continuously removing from the reactor the isocyanate formed during the reaction which is dissolved in the solvent.

In a continuous operation, a degree of concentration of solids occurs in the reactor which can be changed by increasing or decreasing the material added or removed. According to the present invention, the material added consists of amine hydrochloride or its mixture with carbamoyl chloride in a suitable solvent. The material removed contains the isocyanate, which is present in solution in the same solvent, and which is drawn off by the separator mentioned above. Since the reaction rate is increased with an increase of solids, a maximum possible solids concentration is desired which, however, is limited by the fact that a flowing suspension must be maintained. The optimal concentration of solids varies depending upon the amine employed. While, for example, the optimum for 1,5-diamino-2-methylpentane is approximately 20%, the solids concentration for isophoronediamine is only about 1% because the hydrochloride would otherwise form lumps at higher solids concentration levels.

These and other aspects of the invention will become clear to those skilled in the art upon the reading and understanding in the specification.

DESCRIPTION OF THE PREFERRED EMBODIMENTS

The process according to the present invention is particularly efficacious when the hydrochloride method is followed by the procedures discovered in accordance with the present invention and the reaction times can be considerably reduced.

Because of the mild reaction conditions, i.e., low reaction temperature and short reaction time, the isocyanates can be produced in nearly quantitative yield with very high purity.

In the case of the 1,5-diamino-2-methylpentane, the economical production of the corresponding diisocyanate is made possible for the first time. It is possible to reduce the average time of direct contact by the factor 4. In the case of other aliphatic diamines, reaction rates are achieved with the hydrochloride method that previously could only be attained after prephosgenation.

Example 4, however, shows that the process according to the invention can be employed after prephosgenation has already taken place.

According to the process of the present invention, separation of the reaction solution containing isocyanate can take place in various ways. For example, part of the suspension can be shunted from the reactor and the solid matter can be separated and returned to the reactor. The separation can also take place in the reactor itself or before the product output, whereby the solid matter constantly remains in the reactor. Furthermore, the separation can take place by decanting, centrifuging or with a hydrocyclone. The reaction solution in accordance to the present invention is preferably separated with a filter.

The process according to the invention can be employed for phosgenation of primary aliphatic, cycloaliphatic, araliphatic, and aromatic mono- and polyamines having 5 to 18 C atoms or their technical mixture. Representative of such amines are 1,3-bis(aminomethyl)-benzene, aniline, toluylene diamine-1,3 and -1,4, 4,4'-diaminodiphenylmethane, octadecylamine, 1,5,9-triaminoundecane, cyclopentylamine. Representative of aliphatic and cycloaliphatic diamines are 1,6-diaminohexane, 1,5-diamino-2-methylpentane, 1,6-diamino-2,2,4- or -2,4,4-trimethylhexane, 1,9-diamino-5-methylnonane as well as 1-amino-3-aminomethyl-3,5,5- trimethylcyclohexane. The aliphatic and cycloaliphatic diamines are preferred.

Aliphatic and aromatic compounds that are inert under the reaction conditions are suitable as solvents. They contain 6 to 15 C atoms and carry as possible substituents alkyl radicals and chlorine atoms. Representative of exemplary compounds are toluene, xylene, tetralin, and decalin. Chlorobenzene with a boiling point of 130° C. or o-dichlorobenzene with a boiling point of 170° C. are preferable, if the reaction is to be carried out at a higher temperature. The suspension which is subjected to the hot phosgenation contains 3 to 30 liters preferably 10–20 liters, of solvent per kg of amine to be reacted.

One advantage of the present invention is that most of the hydrochlorides and carbamoyl chlorides, especially aliphatic and cycloaliphatic diamines, are so slightly soluble in the aforementioned solvents that they are quantitatively retained by a separator. However, in the event that the amine salts are soluble to a considerable extent in the solvent, they may be removed from the reactor with the nascent isocyanate. In such cases, a secondary reaction is necessary.

The process according to the invention provides advantages even in these cases. For example, the average time of direct contact for the hot phosgenation of toluylene diamine of over 6 hours (example 1 of the DE-OS No. 15 68 844) can be reduced to 2.5 hours (example 6 of the present invention).

After completion of the phosgenation, the reaction solution containing the isocyanate is processed in the customary manner as is also described in the examples.

The diisocyanates according to the invention have a wide variety of utilities and they are especially suitable for the production of polyurethanes, polyureas and polyamides.

The following non-limiting examples are afforded in order that those skilled in the art may more readily understand the present invention and specific preferred embodiments thereof with respect to the process of the present invention in accordance with the foregoing description.

EXAMPLE 1

A 500 ml solution of chlorobenzene containing 45 g of isophoronediamine (1-amino-3-aminomethylene-3,5,5-trimethylcyclohexane), is added and 15 l of HCl gas are introduced every hour into reactor I, a stirrer vessel of 0.5 l volume. The generated hydrochloride suspension continuously overflows into reactor II, a 2-liter volume phosgenation reactor. 50 l of phosgene are passed through every hour at 125° C. At the plate outlet sufficient clear reaction solution (about 500 ml) is removed by a 30-mm diameter glass sinter plate, No. 2 density, to maintain a constant reactor level. After driving off phosgene and hydrochloric acid by distillation under reflux, the solvent is distilled off and the isocyanate is isolated by distillation under reduced pressure. A 1.2% distillation residue remains. The analytical yield amounts to 98.5%.

EXAMPLE 2

A 300 ml solution of chlorobenzene containing 30 g trimethylhexamethylenediamine (isomer mixture 1,6-diamino-2,24(2,4,4)-trimethylhexane) is added and 12 l HCl gas are introduced every hour into reactor I, the apparatus according to example 1. The suspension continuously overflows into reactor II in which hot phosgenation takes place at 122° C. and at a 50 l/h phosgene rate of flow. Every hour sufficient clear reactor solution (about 300 ml) is taken off from the reactor plate so that the reactor level remains constant. Processing takes place as described in example 1. A 1% residue remains in the distillation process. The analytical yield amounts to 98.5% of trimethylhexamethylenediisocyanate.

EXAMPLE 3

As described in example 1, a 300 ml solution of chlorobenzene containing 22.5 g of an isomer mixture of 92% 1,9-diamino-5-methylnonane and 8% 1,8-diamino-2,4-dimethyloctane is added and 9 l of hydrochloric acid gas are introduced every hour. The overflowing suspension is hot phosgenated in reactor II at 122° C. and at a 50 l/h flow rate of phosgene. Sufficient clear reactor solution (about 300 ml) is taken from the reactor plate every hour so that the reactor level remains constant. Processing takes place as described in example 1. A 1.1% residue remains in the distillation process; the analytical yield amounts to 98.5%.

EXAMPLE 4

The phosgenation installation for this example essentially consists of three stirrer vessels connected in series with the following volumes: I=2 liters, II=5 liters, III=30 liters.

In reactor I, 3 liters of chlorobenzene solution containing 150 g of pure 1,5-diamino-2-methylpentane are saturated every hour at 25° C. with excess $CO_2$ for the carbamate suspension.

The carbamate suspension overflows into reactor II in which the carbamylchloride-hydrochloride mixture is formed with excess phosgene at 0° C. Phosgene (phosgene reclaimed from the waste phosgene+fresh phosgene) is introduced at a rate of 200 liters per hour.

Reactor III is operated at 125° C. The phosgene required for hot phosgenation is contained in the reaction suspension overflowing from reactor II. Depending on the amount added, a clear solution of 3 liters is taken off every hour. In front of the plate outlet of the reactor, there is a mesh screen (chrome-nickel steel, mesh width 0.03 mm, 180 cm$^2$ filter surface) that retains all solid parts in the reactor. Under these conditions, a build up of 18% solids occurs in the reactor. Distillation is done in the customary manner for processing.

According to gas chromatography, the crude diisocyanate contains as impurity only 0.1% 1(5)-chlorine-5(1)-isocyanato-2-methylpentane. The distillation residue amounts to 0.8%, the analytical yield, to 99%.

EXAMPLE 5

The phosgenation apparatus of this example consists of two stirrer vessels I and II having a 2 and 30 liter content, respectively, connected in series.

In reactor I, 3 liters of o-dichlorobenzene solution containing 150 g of a technical diamine mixture is saturated hourly with HCl gas at 30° C. The amine mixture constists of the following:
92.3% 1,5-diamino-2-methylpentane
7.3% 1,4-diamino-2-ethylbutane
0.4% 1,6-diaminohexane The hydrochloride suspension continuously overflows into reactor II in which 200 liters per hour of phosgene (reclaimed phosgene and fresh phosgene) are introduced at 140° C. As described in example 4, 3 liters of clear reaction solution are taken off every hour. As a result, 20% solids accumulates in the reactor. According to gas chromatography, the crude diisocyanate contains 0.9% monochloroisocyanates. The distillation residue amounts to 3.7% and the analytical yield is 95%.

EXAMPLE 6

As described in example 1, 1000 ml of chlorobenzene solution containing 100 g of an isomer mixture of 65% 2,4-diaminotoluene and 35% 2,6-diaminotoluene are added every hour and 45 l of hydrochloric acid are introduced. The overflowing suspension is hot phosgenated in reactor II at 120° C. and with 70 l/h phosgene introduced. On the reactor plate, sufficient clear reaction solution (about 1,000 ml/h), is taken off by a glass sinter plate, No. 3 density, to maintain the reactor level at a constant. The clear reaction solution passes through a heated plate column with 5 plates and a hold-up totaling 500 ml. At 125° C., 30 l per hour of phosgene are passed countercurrent from the bottom to the top. Further processing takes place as described in example 1. A 6.6% residue remains in the distillation process; the analytical yield amounts to 93.2%.

While the invention has been described and illustrated with reference to certain preferred embodiments thereof, those skilled in the art will appreciate that various changes, modifications and substitutions can be made therein without departure from the spirit of the invention. For example, temperature ranges and feed ratios other than the preferred range as set forth hereinabove may be applicable as a consequence of the nature of various reactants employed in the process and such other expected variations or differences in results are contemplated in accordance with the objects and practices of the present invention. It is intended, therefore, that the invention be limited only by the scope of the claims which follow.

What is claimed as new and desired to be secured by Letters Patent of the United States is:

1. A process for producing organic isocyanates in high yields and of high purity by a continuous hot phosgenation reaction comprising continuously feeding into a reactor phosgene and a solvent containing either (i) an amine hydrochloride or (ii) a carbamoyl chloride-hydrochloride mixture while continuously removing, from said reactor, solvent containing the organic isocyanate thereby produced, wherein the total quantity of solids consisting of either (i) or (ii) are essentially retained in the reactor by a separator.

2. The process according to claim 1, wherein said carbamoyl chloride-hydrochloride mixute is produced by saturating a primary aliphatic diamine having 5–12 carbon atoms with carbon dioxide.

3. The process of claim 2, wherein said primary aliphatic diamine is 1,5-diamino-2-methylpentane.

4. The process acdording to claim 1 wherein said separator is a filter.

5. The process according to claim 1 wherein the solids are maintained at a constant concentration by varying the amount of (a) phosgene and (b) either amine hydrochloride or carbamoyl chloride - hydrochloride mixture added to or (c) isocyanate removed from the reactor.

6. The process according to claim 5 wherein said solids are maintained at a concentration range from about 3% to about 30%.

7. The process according to claim 6 wherein said solids are maintained at a concentration range from about 10% to about 20%.

8. The process according to claim 1 wherein said hot phosgenation reaction is conducted at a temperature of about 80° C. to about 200° C.

9. The process according to claim 1 wherein said hot phosgenation reaction is conducted at a temperature of about 80° C. to about 200° C.

10. The process according to claim 1 wherein said amine hydrochloride is a hydrochloride of a primary aliphatic diamine having 5-12-carbon atoms.

11. The process according to claim 1 wherein primary aliphatic diamines with 5–12-carbon atoms are phosgenated.

12. The process according to claim 1 wherein said amine hydrochloride is in admixture with carbamoyl chloride in a suitable solvent.

* * * * *